(12) United States Patent
Brandstaetter et al.

(10) Patent No.: US 12,042,344 B2
(45) Date of Patent: Jul. 23, 2024

(54) MEDICAL OR DENTAL TREATMENT DEVICE AND TOOL FOR SUCH A TREATMENT DEVICE

(71) Applicant: W&H Dentalwerk Bürmoos GmbH, Bürmoos (AT)

(72) Inventors: Andreas Brandstaetter, St. Pantaleon (AT); Christian Pruckner, Vienna (AT); Theresa Auer, Oberndorf (AT); Johann Eibl, Mattighofen (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 685 days.

(21) Appl. No.: 17/003,879

(22) Filed: Aug. 26, 2020

(65) Prior Publication Data

US 2020/0390519 A1     Dec. 17, 2020

Related U.S. Application Data

(63) Continuation of application No. 15/640,165, filed on Jun. 30, 2017, now abandoned.

(30) Foreign Application Priority Data

Jul. 4, 2016    (EP) .................................. 16177709

(51) Int. Cl.
*A61C 1/00*     (2006.01)
*A61B 17/00*    (2006.01)
(Continued)

(52) U.S. Cl.
CPC ............ *A61C 1/0015* (2013.01); *A61B 17/00* (2013.01); *A61B 17/1622* (2013.01);
(Continued)

(58) Field of Classification Search
CPC ... A61C 1/0007; A61C 1/0015; A61C 17/221; A61C 17/20; A61C 2204/005;
(Continued)

(56) References Cited

U.S. PATENT DOCUMENTS

2005/0033544 A1    2/2005  Brooks et al.
2008/0293008 A1   11/2008  Regere et al.
(Continued)

FOREIGN PATENT DOCUMENTS

DE        3708801       9/1988
DE      102006057338    6/2008
(Continued)

OTHER PUBLICATIONS

European Search Report for EP16177709 (mailed Jan. 10, 2017).
Translation of DE3708801 (Jan. 2019).

*Primary Examiner* — Edward Moran
(74) *Attorney, Agent, or Firm* — Klarquist Sparkman, LLP

(57) ABSTRACT

A medical or dental treatment device comprises a tool retainer, a measuring coil and an evaluation device. The tool retainer can be connected to a plurality of different tools. The measuring coil can be supplied with a periodic electrical energy. The evaluation device can be connected to the measuring coil for detecting whether a tool is connected to the treatment device or which of a plurality of tools is connected to the treatment device. On the basis of an electromagnetic (e.g., inductive) coupling between the tool accommodated in the tool retainer and the measuring coil supplied with the periodic energy, a periodic measurement signal specific to each tool can be generated and assigned by the evaluation device to the tool. The evaluation device determines the phase shift of the electrical voltage and of the electric current of the periodic measurement signal.

19 Claims, 3 Drawing Sheets

(51) Int. Cl.
  *A61B 17/16* (2006.01)
  *A61B 18/00* (2006.01)
  *A61B 34/00* (2016.01)
  *A61B 90/90* (2016.01)
  *A61B 90/98* (2016.01)
  *A61C 1/08* (2006.01)
  *A61C 1/14* (2006.01)
  *A61C 17/20* (2006.01)
  *A61C 17/22* (2006.01)

(52) U.S. Cl.
  CPC .............. *A61B 90/90* (2016.02); *A61B 90/98* (2016.02); *A61C 1/088* (2013.01); *A61C 1/145* (2013.01); *A61C 17/20* (2013.01); *A61C 17/221* (2013.01); *A61B 2017/00464* (2013.01); *A61B 2018/00869* (2013.01); *A61B 2018/00892* (2013.01); *A61B 2034/256* (2016.02); *A61C 2204/005* (2013.01)

(58) Field of Classification Search
  CPC .................. A61B 90/90; A61B 90/98; A61B 2017/00464; A61B 2018/00869
  See application file for complete search history.

(56) References Cited

U.S. PATENT DOCUMENTS

| | | |
|---|---|---|
| 2010/0109644 A1 | 5/2010 | Pruckner et al. |
| 2015/0150647 A1 | 6/2015 | Chevalier |

FOREIGN PATENT DOCUMENTS

| | | |
|---|---|---|
| EP | 2184028 | 5/2010 |
| GB | 2382876 | 6/2003 |
| JP | S5537936 | 3/1980 |
| JP | 2004518511 A | 6/2004 |
| JP | 2010519522 | 6/2010 |

MEDICAL OR DENTAL TREATMENT DEVICE AND TOOL FOR SUCH A TREATMENT DEVICE

CROSS REFERENCE TO RELATED APPLICATION

The present application is a continuation of U.S. patent application Ser. No. 15/640,165, filed Jun. 30, 2017, which claims priority from pending European Patent Application No. 16177709.9, filed Jul. 4, 2016, which is incorporated herein by reference.

BACKGROUND

Field

The present invention relates to a medical or dental treatment device which can be connected to a plurality of different tools, wherein the medical or dental treatment device is provided with an evaluation device for detecting whether one of the plurality of tools is connected to the treatment device or which of the plurality of tools is connected to the treatment device. The invention also refers to a corresponding method and tools which can be distinguished with a medical or dental treatment device of this type.

Description of Prior Art

A medical or dental treatment device of this type is known from patent application US 2010/109644 A1. This treatment device which comprises an evaluation device for detecting whether one of the plurality of tools is connected to the treatment device or which of the plurality of tools is connected to the treatment device functions extremely well and is held in high esteem by users.

SUMMARY

Based on the foregoing it would be advantageous to provide a treatment device with an evaluation device which has been further developed to function more effectively, including such that a larger number of tools or tool groups can be distinguished. Accordingly, it is also an aim of the present invention to provide a method and a tool that function more effectively and with which a larger number of tools or tool groups can be distinguished.

The medical or dental treatment device in accordance with the invention, which can be connected to a plurality of different tools, comprises a tool retainer for connecting the treatment device to a tool, at least one measuring coil which is connected to an electrical energy supply device via an electrical line and can be supplied with a periodic, in particular sinusoidal, electrical energy supply (alternating current) from the electrical energy supply device, and an evaluation device electrically connected to the at least one measuring coil for detecting whether a tool is connected to the treatment device or which of a plurality of tools is connected to the treatment device. Due to an electromagnetic, in particular inductive, coupling between the tool accommodated in the tool retainer and the at least one measuring coil supplied with the periodic, in particular sinusoidal energy, a periodic, in particular sinusoidal measurement signal can be generated which is specific to each tool and can be assigned to the respective tool by the evaluation device.

In accordance with a first embodiment, the evaluation device for detecting whether a tool is connected to the treatment device or which of a plurality of tools is connected to the treatment device determines the phase shift or phase displacement of the electrical voltage and of the electric current of the periodic, in particular sinusoidal measurement signal.

In accordance with a second embodiment, the medical or dental treatment device comprises at least one tool as well as the components mentioned above, namely the tool retainer, at least one measuring coil, and an evaluation device for detecting whether a tool is connected to the treatment device or which of a plurality of tools is connected to the treatment device which is electrically connected to the at least one measuring coil. The at least one tool comprises a tool shaft and a working end connected to the tool shaft for working on a treatment site, wherein the tool shaft comprises an electrically conductive identification element in which due to the electromagnetic, in particular inductive coupling between the tool accommodated in the tool retainer and the at least one measuring coil supplied with the periodic, in particular sinusoidal energy, an (induced) alternating electric current and/or electrical eddy currents can be induced which feeds back onto or affects the periodic, in particular sinusoidal electrical energy flowing in the at least one measuring coil to generate the periodic, in particular sinusoidal measurement signal which can be assigned to the respective tool, in particular by mutual inductance and/or ohmic losses. The acting on the periodic, in particular sinusoidal electrical energy flowing in the at least one measuring coil takes place in particular indirectly through the changing magnetic fields and/or electric fields of the alternating electric current and/or the electrical eddy currents.

As will be described below in more detail, the detection or determination of a plurality of tools which can be connected to the medical or dental treatment device is in particular based on the fact that each tool has a specific electrically conductive identification element, i.e., an electrically conductive identification element with at least one individual property or an individual parameter. This individual property or this individual parameter causes an effect or a feed back onto the periodic, in particular sinusoidal electrical energy flowing in the at least one measuring coil which is specific to that identification element, whereupon the periodic, in particular sinusoidal measurement signal which is uniquely assignable or specific to the respective tool can be generated. The evaluation device or a comparator is in particular configured such that it can compare this received specific periodic, in particular sinusoidal measurement signal with predetermined comparative values which, for example, are stored in a memory of the evaluation device, and can detect the tool accommodated in the tool retainer.

Preferably, in addition to the phase shift of the periodic, in particular sinusoidal measuring signal, the evaluation device for determining whether a tool is connected to the treatment device or which of a plurality of tools is connected to the treatment device determines the amplitude, in particular the extreme values of the amplitude, of the electrical voltage of the periodic, in particular sinusoidal measurement signal. This further increases the number of tools or tool groups which can be distinguished from each other.

For each of the two embodiments individually, i.e., determining the phase shift of the electrical voltage and the electric current of the periodic, in particular sinusoidal measurement signal as well as providing a tool with an electrically conductive identification element in which an alternating electric current and/or electrical eddy currents can be induced, a larger number of tools or tool groups can be distinguished. Particularly preferably, both embodiments are combined together, in particular in a medical or dental treatment device, whereupon the number of tools or tool groups which can be distinguished from each other can be increased substantially further. Starting from the number of mutually distinguishable tools or tool groups known from the prior art, in experiments when applying only one of the two embodiments, the number of reliably mutually distinguishable tools or tool groups was increased by approximately 66%, and when using both embodiments together, an approximately 3- to 6-fold increase was observed.

Preferably, at least the measuring coil and the evaluation device, in particular also the electrical energy supply device form an electrical measurement circuit for detecting whether a tool is connected to the treatment device or which of a plurality of tools is connected to the treatment device. Preferably, the electrical measurement circuit comprises further components, for example filters or amplifiers, in particular for the periodic, in particular sinusoidal measurement signal, a microcontroller, a comparator to compare the periodic, in particular sinusoidal measurement signal received by the evaluation device or a signal derived therefrom with predetermined comparative values in order to assign the periodic, in particular sinusoidal measurement signal to a tool, in particular to the tool accommodated in the tool retainer, and/or a display to advise the user about the name of the tool or about operational data for the tool, in particular the tool accommodated in the tool retainer.

Preferably, the evaluation device is configured to receive and evaluate the periodic, in particular sinusoidal measurement signal generated in or at the measuring coil, in order to detect whether a tool is connected to the treatment device or which of a plurality of tools is connected to the treatment device. Particularly preferably, the evaluation device or a microcontroller of the treatment device comprises a computer program with programming code means for carrying out a method for detecting whether a tool is connected to a treatment device or which of a plurality of tools is connected to the treatment device, as described below. The method or the computer program is preferably implemented in software.

Preferably, the medical or dental treatment device comprises a medical or a dental handpiece or contra-angle handpiece and a control device, which in particular are designed to be separate and/or are connected together via a tube. Preferably, at least a portion of the evaluation device is provided in the control device and/or is configured as a part of the control device. Preferably, further components are provided at the control device, for example actuators so that the operator can select and/or adjust operational parameters and/or operating resources and/or quantities of operating resources, a display and/or a liquid supply unit which is configured to supply a treatment liquid, in particular for dispensing onto a treatment site to the handpiece or contra-angle handpiece. Preferably, the force-fit or positive tool retainer is disposed on or in the handpiece or contra-angle handpiece in an interlocked or friction-fitted manner. Preferably, the medical or dental treatment device is configured as a table top device.

Preferably, the medical or dental treatment device comprises a drive unit which is configured to set the tool connected to the treatment device into a drive movement, for example a rotary and/or oscillating and/or vibrating drive movement. Preferably, the drive unit is disposed in the handpiece or contra-angle handpiece or is attached thereto. Particularly preferably, the drive unit comprises an air motor or an electric motor or a pneumatic, piezoelectrical or magnetostrictive oscillatory drive.

Preferably, the medical or dental treatment device comprises a device for removing tartar, plaque, biofilm and/or stains on teeth with a pneumatic, piezoelectrical or magnetostrictive sonic or ultrasonic vibrational drive which is frequently known as a scaling device. Alternatively, the medical or dental treatment device comprises other devices for restoration, prosthetics, endodentistry, implantology or other applications, in particular with a tool which can be made to move in a turning or rotary movement.

Accordingly, the tool is preferably configured as a rotary tool, as an oscillating tool, as a tool that can be made to vibrate, as a sonically or ultrasonically driven tool or as a tartar-removing tool.

Preferably, the measuring coil is disposed in the handpiece or contra-angle handpiece, in particular on or adjacent to the tool retainer. In particular, the measuring coil is configured and/or is disposed in the handpiece or contra-angle handpiece such that the electrically conductive identification element can be positioned in the measuring coil, in particular when the tool is accommodated or held in the tool retainer.

The electrical energy supply device is preferably configured to generate periodic, in particular sinusoidal electrical energy (alternating current) and to supply the at least one measuring coil with periodic, in particular sinusoidal electrical energy (alternating current). The electrical energy supply device can either be provided in the medical or dental treatment device, in particular in the control device, or outside the medical or dental treatment device. Disposing the electrical energy supply device in the treatment device, in particular in a microcontroller or as part of a microcontroller unit, advantageously facilitates the determination of the phase shift of the electrical voltage and of the electric current of the periodic, in particular sinusoidal measurement signal, because the evaluation unit knows the zero point of the periodic, in particular sinusoidal electrical energy which is required for determining the phase shift, or it can readily be determined by the evaluation unit. Particularly preferably, the electrical energy supply device is configured as a part of a microcontroller or a microcontroller unit of the treatment device and/or is controlled by a microcontroller of the treatment device by software. Particularly preferably, the electrical energy supply device comprises a signal generator.

The electromagnetic, in particular inductive coupling between the tool accommodated in the tool retainer and the at least one measuring coil supplied with the periodic, in particular sinusoidal energy for producing a periodic, in particular sinusoidal measurement signal which is specific to each tool and which can be assigned to the respective tool by the evaluation device comprises, for example, affecting or modifying the inductance of the at least one measuring coil which, for example, is caused by the soft magnetic properties of the tool and/or the electrically conductive identification element. The electromagnetic, in particular inductive coupling additionally or alternatively also comprises generating the periodic, in particular sinusoidal measurement signal which is specific to each tool by mutual inductance and/or ohmic losses which, for example, are caused by an alternating current and/or eddy currents induced in the tool and/or the electrically conductive identification element and the resulting varying magnetic fields or electrical fields.

The periodic, in particular sinusoidal electrical energy made available from the electrical energy supply device in particular forms the output signal or the basis for the periodic, in particular sinusoidal measurement signal. Because of the electromagnetic, in particular inductive coupling between the tool accommodated in the tool retainer and the at least one measuring coil, at least one parameter of the periodic electrical energy, for example the electrical voltage, the electric current or the amplitude of the electrical voltage, is influenced or modified and thus the periodic, in particular sinusoidal measurement signal which is specific to each of the plurality of tools is generated.

The at least one tool preferably comprises a tool shaft and a working end connected to the tool shaft for working on a treatment site. The tool shaft is preferably cylindrical in shape. Preferably, at least one geometric structure is provided on the tool shaft to connect with the tool retainer and/or to engage a retaining element of the tool retainer, for example a thread, a recess or an indentation. The working end of the tool is preferably abrasive in configuration and, for example, comprises at least one cutting edge and/or abrasive particles.

Preferably, the at least one electrically conductive identification element of the tool shaft comprises a material with a high electrical conductivity, in particular a metallic material, for example copper, gold, silver, tin, tungsten or a metal alloy, preferably with at least one of the metals mentioned above, for example brass, bronze or nickel silver.

Preferably, the at least one electrically conductive identification element is provided on a base material of the tool shaft, wherein the at least one electrically conductive identification element and the base material comprise different materials. Preferably, the base material of the tool shaft comprises a plastic or a metallic material, for example steel. Alternatively, it is also possible for the at least one electrically conductive identification element and the tool shaft to be produced from the same material and/or to be formed as one piece.

Preferably, the at least one electrically conductive identification element comprises a wire, a film, layer, sleeve, winding or coil or is configured as such. Preferably, the at least one electrically conductive identification element, in particular the wire, the film, sleeve, winding or coil is fastened by bonding, pressing, shrink fitting, screwing or welding to the tool, preferably in an non-releasable manner.

Alternatively, the at least one electrically conductive identification element comprises a coating or is configured as such. Preferably, the coating is produced by chemical or galvanic deposition of the material of the at least one electrically conductive identification element onto the tool. Particularly preferably, the at least one electrically conductive identification element comprises a winding or coil which is produced by coating the tool with the material of the at least one electrically conductive identification element and subsequent mechanical, chemical or laser processing of the coating in order to remove a portion of the coating in order to obtain the winding or coil in this manner.

Alternatively, the at least one electrically conductive identification element is provided with a plastic sleeve with a metallic coating provided thereon which can be fixed on the tool, for example by bonding, pressing, shrink fitting or screwing. In this manner, it is advantageously possible to use the same material, in particular metallic material, for the base material of the tool or the tool shaft and for the at least one electrically conductive identification element.

Preferably, the at least one electrically conductive identification element, in particular when it is configured as a coating, layer or film, is covered with an additional layer provided on or deposited onto the tool. The at least one electrically conductive identification element is thus in particular disposed between this additional layer and the base material of the tool shaft The additional layer preferably forms a protective layer with a higher resistance compared with the material of the at least one electrically conductive identification element, for example against corrosion or mechanical stresses, a passivation layer of the material of the at least one electrically conductive identification element, for example in the form of an oxide layer, or an optical barrier in order to conceal the presence of the at least one electrically conductive identification element.

Preferably, the at least one electrically conductive identification element forms a closed electrical circuit surrounding the tool shaft, in which a (regularly, periodically changing polarity) alternating electric current can flow, in particular about the tool shaft or about the longitudinal axis of the tool shaft. Preferably, the alternating electric current flows as a ring current in the electrically conductive identification element about the tool shaft or about a longitudinal axis of the tool shaft. Preferably, the electrically conductive identification element is configured as a self-contained (i.e., endless) coil, winding, wire, film or coating, in order to form the closed electrical circuit. In order to detect different tools, surprisingly, a single turn or winding of the coil, winding, wire, film or coating (going 360° around the tool shaft) is sufficient to form the closed electrical circuit. Particularly preferably and surprisingly, this single turn or winding may also be in the shape of a sleeve or be a sleeve, so that the at least one electrically conductive identification element can in particular also have a cylindrical sleeve in order to form a closed electrical circuit about the tool shaft.

Such a self-contained electrical circuit formed by the at least one electrically conductive identification element, in particular the (induced) alternating current or ring current flowing in it, bring about due to the electromagnetic, in particular inductive coupling, a particularly effective feedback onto the periodic, in particular sinusoidal electrical energy flowing in the at least one measuring coil, in particular through mutual inductance, in order to generate the periodic, in particular sinusoidal measurement signal which can be assigned to the respective tool.

Alternatively, the at least one electrically conductive identification element comprises two electrically separated ends. Accordingly, the at least one electrically conductive identification element does not form a closed electrical circuit. Thus, in an identification element of this type, a (regularly, periodically polarity-changing) alternating electric current or a ring current flowing about the tool shaft or about a longitudinal axis of the tool shaft cannot be induced, but only electrical eddy currents can be induced therein. Surprisingly, it has been found out that these electrical eddy currents are also capable of producing the desired detection or differentiation between a plurality of different tools by modifying or manipulating the periodic, in particular sinusoidal electrical energy flowing in the at least one measuring coil, in particular by ohmic losses.

The at least one electrically conductive identification element with two electrically separated ends comprises, for example, a split sleeve, a coil, a winding or a wire with two free or electrically unconnected ends, a coating which is split like the sleeve or a coating corresponding to the winding or the wire with two free or electrically unconnected ends. In particular, the two electrically separated ends are formed by a gap or slit between these two ends.

Preferably, the medical or dental treatment device comprises a plurality of different tools each of which having a tool shaft with at least one electrically conductive identification element. Preferably, this plurality of different tools is collected together in a set of tools. As already described above, the detection or differentiation of this plurality of tools which can be connected to the medical or dental treatment device, is based on the fact that each tool has a specific electrically conductive identification element, i.e., an electrically conductive identification element with at least one individual property or an individual parameter.

Preferably, the electrically conductive identification elements of the tools, in particular of the set of tools, differ by at least one of the following parameters:

- the axial length of the electrically conductive identification elements with respect to a longitudinal axis of the tool shaft; preferably, the axial length of an electrically conductive identification element is between 0.5 mm and 10 mm; preferably, the axial length of electrically conductive identification elements, in particular of a set of tools, (respectively) differ by 0.5 mm, 1 mm, 1.5 mm, 2 mm, 2.5 mm, 5 mm or 10 mm;
- the cross-sectional areas or wire diameters of the electrically conductive identification element, in particular the cross-sectional areas or wire diameter of windings, coils or wires; preferably, the cross-sectional area or wire diameter of an electrically conductive identification element is between 0.05 mm and 1 mm; preferably, the cross-sectional areas or wire diameters, in particular of a set of tools, (respectively) differ by 0.05 mm, 0.1 mm, 0.15 mm, 0.2 mm, 0.25 mm or 0.5 mm;
- the thicknesses of the electrically conductive identification elements transversely or radially to a longitudinal axis of the tool shaft; preferably, the thickness of an electrically conductive identification element is between 0.03 mm and 1 mm, preferably 0.05 mm to 0.5 mm; preferably, the thicknesses, in particular of a set of tools, (respectively) differ by 0.05 mm, 0.1 mm, 0.15 mm, 0.2 mm, 0.25 mm or 0.5 mm;
- the layer thicknesses of the electrically conductive identification elements deposited on the tool shafts; preferably, the layer thickness of an electrically conductive identification element is between 0.03 mm and 1 mm, preferably 0.05 mm and 0.5 mm; preferably, the layer thicknesses, in particular of a set of tools, (respectively) differ by 0.05 mm, 0.1 mm, 0.15 mm, 0.2 mm, 0.25 mm or 0.5 mm;
- the materials of the electrically conductive identification elements; preferably, at least one electrically conductive identification element of a tool comprises a material which differs from a material of an electrically conductive identification element of another tool; as an example, an electrically conductive identification element comprises copper, gold, silver, tin, tungsten or a metal alloy, preferably with at least one of the metals mentioned above, for example brass, bronze or nickel silver;
- the number of turns and/or lengths of the electrically conductive identification elements formed as coils or windings; preferably, the number of turns of an electrically conductive identification element is between one and 50 turns; preferably, the number of turns, in particular of a set of tools, (respectively) differ by 1, 2, 3, 4, 5, 6, 7, 8, 9 or 10 turns.

Preferably (in addition to the electrically conductive identification element), an alternating electric current and/or electrical eddy currents is/are inducible in the base material of the tool, in particular the tool shaft, through the electromagnetic, in particular inductive coupling between the tool accommodated in the tool retainer and the at least one measuring coil supplied with the periodic, in particular sinusoidal energy, which also contribute to the generation of the periodic, in particular sinusoidal measurement signal which can be assigned to the respective tool, in particular by modifying the periodic, in particular sinusoidal electrical energy flowing in the at least one measuring coil by mutual inductance and/or ohmic losses.

Preferably, for detection of or differentiation between the plurality of tools, in particular of the set of tools, by the evaluation device they differ in at least one of the following parameters:

- the base material of the tool shaft; as an example, at least one tool comprises a base material formed from metal or plastic; as an example, at least one tool comprises a base material formed from a first metal or a first metal alloy and another tool has a base material formed from a second, different metal or from a second, different metal alloy;
- the diameter of at least one section of the tool shaft; preferably, the diameters of at least sections of a plurality of different tool shafts, in particular of a set of tools, (respectively) differ by 0.05 mm, 0.1 mm, 0.15 mm, 0.2 mm;
- the length of the tool shaft; preferably, the lengths of a plurality of different tool shafts, in particular of a set of tools, (respectively) differ by 0.05 mm, 0.1 mm, 0.15 mm, 0.2 mm.

Preferably, the tool shaft of the at least one tool or of at least one tool of a set of tools has a plurality of, at least two or three or four electrically conductive and separated identification elements. In this manner, an even more reliable identification of a tool and/or detection and differentiation of an even larger number of tools is made possible. The separated identification elements comprise, for example, a wire, a winding, coil, coating, film, layer or sleeve.

The plurality of separated identification elements of a tool shaft may have identical elements (for example two or more wires, windings, coils, coatings, films, layers or sleeves) or different elements (for example a sleeve and a winding, or a film and a coil). Each of the plurality of separated identification elements of a tool shaft may form a closed electrical circuit surrounding the tool shaft, in which the alternating electric current can flow, in particular about the tool shaft or about a longitudinal axis of the tool shaft, or have two electrically separated ends. Alternatively, the plurality of separated identification elements of a tool shaft differ in that at least one of the identification elements forms a closed electrical circuit and at least one other of the identification elements has two electrically separated ends.

Preferably, the medical or dental treatment device comprises a plurality of measuring coils (or one measuring coil with at least three connections) which are electrically connected to the evaluation device for determining whether a tool is connected to the treatment device or which of a plurality of tools is connected to the treatment device, so that in particular the evaluation device can receive a plurality of periodic, in particular sinusoidal measurement signals from the plurality of measurement coils, in order to be able to distinguish between and detect the plurality of tools. This is of particular advantage when the tool shaft of at least one tool, in particular of a set of tools, has a plurality of, at least two, electrically conductive and separated identification elements. Preferably, each measuring coil is associated with one of the plurality of separated identification elements, in particular when the tool is accommodated in the tool retainer.

Preferably, the medical or dental treatment device is configured to supply the plurality of measuring coils temporally sequentially with periodic, in particular sinusoidal electrical energy (alternating current), so that in particular, a plurality of temporally offset periodic, in particular sinusoidal measurement signals can be produced and/or be evaluated by the evaluation device in order to detect a tool. Alternatively, the medical or dental treatment device is configured to supply the plurality of measuring coils simultaneously with periodic, in particular sinusoidal electrical energy (alternating current) in order to produce a plurality of periodic, in particular sinusoidal measurement signals which will be analysed by the evaluation device in order to detect a tool.

Alternatively or in addition, it is also possible for the medical or dental treatment device or the evaluation device to be configured so as to interconnect at least two of the plurality of measuring coils for electromagnetic, in particular inductive coupling with the tool accommodated in the tool retainer, in particular with the at least one electrically conductive identification element. This can be envisaged, for example, when a set of tools has at least one tool with one electrically conductive identification element and at least one tool with a plurality of electrically conductive identification elements: for electromagnetic, in particular inductive coupling with the tool with one electrically conductive identification element, the plurality of measuring coils are interconnected and for electromagnetic, in particular inductive coupling with the tool with a plurality of electrically conductive identification elements, the plurality of measuring coils are not interconnected or, as described above, each measuring coil is associated with one of the plurality of separated identification elements.

Clearly, it is also possible to set up an electromagnetic, in particular inductive coupling with a tool with a plurality of electrically conductive identification elements and only one measuring coil and to correctly identify the tool, or to set up an electromagnetic, in particular inductive coupling with a tool with only one electrically conductive identification element and a plurality of measuring coils, and to correctly identify the tool.

Preferably, the medical or dental treatment device, in particular the electric energy supply device, is configured in order to detect whether a tool is connected to the treatment device or which of a plurality of tools is connected to the treatment device, to supply the at least one measuring coil with periodic, in particular sinusoidal electrical energy (alternating current) at different frequencies, whereupon detection or differentiation of the tools becomes more reliable. Preferably, the electrical energy supply device is a part of a microcontroller or a microcontroller unit of the treatment device, wherein the at least one measuring coil is supplied with periodic, in particular sinusoidal electrical energy at different frequencies via software) under the control of the microcontroller. Alternatively, it is also possible for the medical or dental treatment device to comprise a frequency modulator which is electrically connected to the electrical energy supply device and the at least one measuring coil, which modifies the frequency of the periodic electrical energy output to the at least one measuring coil.

Preferably, the treatment device or the frequency modulator is configured to supply the at least one measuring coil with periodic, in particular sinusoidal electrical energy with different frequencies or frequency ranges in a manner such that different physical effects influence (variably intensely) the generation of the periodic, in particular sinusoidal measurement signal, so that the detection or differentiation of a tool becomes even more reliable: preferably, a frequency is selected, for example from a frequency range of less than 500 Hz, such that the generation of the periodic, in particular sinusoidal measurement signal is primarily caused by inductance or soft magnetic properties of the tool (of the base material and/or of the electrically conductive identification element); preferably, a frequency is selected, for example from a frequency range between 1 kHz and 200 kHz, in a manner such that the generation of the periodic, in particular sinusoidal measurement signal is primarily produced by mutual inductance of the tool (in particular of the electrically conductive identification element); preferably, a frequency is selected, for example from a frequency range of more than 200 kHz, in a manner such that the generation of the periodic, in particular sinusoidal measurement signal is primarily caused through the induced eddy currents (in particular in the electrically conductive identification element). Preferably, at least two of these three frequencies or frequency ranges mentioned are pre-set or stored in the treatment device, for example the evaluation device or a control device, so that the at least one measuring coil can, preferably automatically, be supplied with periodic, in particular sinusoidal electrical energy at the appropriate frequencies.

Alternatively, the treatment device or the frequency modulator is configured to supply the at least one measuring coil with periodic, in particular sinusoidal electrical energy at different frequencies from at least one of the frequency ranges mentioned above. Particularly preferably, the treatment device or the frequency modulator is configured to supply the at least one measuring coil with periodic, in particular sinusoidal electrical energy (alternating current) at at least two different frequencies in the range from approximately 1 kHz to approximately 60 kHz. In this manner, advantageously, detection and differentiation of tools is possible while avoiding disruptive effects, for example too much heating of the treatment device.

Alternatively, the treatment device or the frequency modulator is configured to supply the at least one measuring coil with periodic, in particular sinusoidal electrical energy at only one frequency, for example in the range from approximately 1 kHz to approximately 150 kHz, preferably approximately 1 kHz to approximately 60 kHz. Generation of the periodic, in particular sinusoidal measurement signal here is primarily caused by the mutual inductance of the tool (in particular of the electrically conductive identification element) and to a lesser extent by eddy currents.

Preferably, the treatment device or the evaluation device is configured to analyse the periodic, in particular sinusoidal measurement signal which can be assigned to the respective tool using Fourier transformation, so that the periodic, in particular sinusoidal measurement signal can in particular be assigned to a specific tool.

In accordance with one embodiment, a method is provided for detecting whether a tool is connected to a treatment device or which of a plurality of tools is connected to the treatment device, in which the at least one measuring coil is supplied with periodic, in particular sinusoidal electrical energy (alternating current), a periodic, in particular sinusoidal measurement signal which is specific for each tool and which can be assigned to the respective tool by the evaluation device is generated (in the measuring coil) on the basis of an electromagnetic, in particular inductive coupling between the tool accommodated in the tool retainer and the at least one measuring coil supplied with the periodic, in particular sinusoidal energy, wherein said periodic, in particular sinusoidal measurement signal is received by the evaluation device (via the electrical connection with the measuring coil), and wherein in order to detect whether a tool is connected to the treatment device or which of a plurality of tools is connected to the treatment device, the evaluation device determines the phase shift of the electrical voltage and the electric current of the periodic, in particular sinusoidal measurement signal. Preferably, in order to detect whether a tool is connected to the treatment device or which of a plurality of tools is connected to the treatment device, the evaluation device also determines the amplitude, in particular the extreme values of the amplitude, of the electrical voltage of the periodic, in particular sinusoidal measurement signal.

In accordance with another embodiment, a method is provided for detecting whether a tool is connected to a treatment device or which of a plurality of tools is connected to the treatment device, in which, in the at least one electrically conductive identification element of the at least one tool, on the basis of the electromagnetic, in particular inductive coupling between this tool accommodated in the tool retainer and the at least one measuring coil supplied with the periodic, in particular sinusoidal energy, an alternating electric current and/or electrical eddy currents is induced which feeds back onto or influences the periodic, in particular sinusoidal electrical energy flowing in the at least one measuring coil to generate the periodic, in particular sinusoidal measurement signal which can be assigned to the respective tool, in particular by mutual inductance and/or ohmic losses.

Preferably, in order to detect whether a tool is connected to the treatment device or which of a plurality of tools is connected to the treatment device, the at least one measuring coil is provided with periodic, in particular sinusoidal electrical energy (alternating current) at different frequencies, as already described in detail above.

Preferably, the alternating electric current (regularly, periodically changing its polarity) induced by the electromagnetic, in particular inductive coupling between the tool accommodated in the tool retainer and the at least one measuring coil supplied with the periodic, in particular sinusoidal energy, flows about the tool shaft or about a longitudinal axis of the tool shaft, particularly in the at least one electrically conductive identification element. Preferably, to this end, the at least one electrically conductive identification element is configured as a closed electrical circuit, as has already been described in detail above.

Preferably, the tool shaft of the at least one tool comprises at least two electrically conductive and separated identification elements in which, preferably sequentially, in order to detect whether a tool is connected to the treatment device or which of a plurality of tools is connected to the treatment device, alternating electric current and/or electrical eddy currents is/are induced, as already described in detail above.

Preferably, the treatment device has a plurality of measuring coils which are electrically connected to the evaluation device and which, in order to detect whether a tool is connected to the treatment device or which of a plurality of tools is connected to the treatment device, are, preferably sequentially, supplied with periodic, in particular sinusoidal electrical energy (alternating current), as already described in detail above.

Preferably, the treatment device operates the medical or dental tool connected to the tool retainer and identified by the evaluation device using appropriate operational parameters and/or appropriate resources and/or quantities of resources.

The detection and differentiation of the various tools is preferably provided to supply the treatment device, in particular the handle element, the drive unit or the tool, with appropriate resources or quantities of resources or to operate it with appropriate operational parameters. In this regard, for example, tools which are driven by vibrations have different resonance frequencies, wherein the drive unit generating the vibrations is supplied with different supply voltages depending on the tool attached to the treatment device, so that the attached tool can be operated as precisely as possible with its resonance frequency. Preferably, the treatment device is configured as a tartar removal or scaling device which has a drive unit comprising an oscillator, in particular a piezoelectric oscillator, which can be supplied with drive energy, drive power or drive voltage depending on the tool connected to the treatment device and detected by the evaluation device.

Preferably, the treatment device, for example the evaluation device or a control device or supply unit of the treatment device, comprises at least one actuator, for example a valve, and/or at least one control or regulating element which operates the identified medical or dental tool with appropriate operational parameters and/or with appropriate resources and/or quantities of resources.

Preferably, different tools require different coolants or quantities of coolant, so that the treatment device is configured to dispense appropriate coolants or quantities of coolant onto the tool.

In order that the tool can be supplied with the appropriate operational parameters, resources or quantities of resources, after detection of the tool attached to the treatment device, the evaluation device is preferably configured to output a specific control signal for each tool to a control device or supply unit. In this regard, the evaluation device is preferably provided with a memory in which a characteristic value is stored for each tool, in particular a characteristic value for the phase shift, and additionally in particular also an amplitude value for the voltage of the periodic, in particular sinusoidal measurement signal or a value derived therefrom, and a comparator which, in order to identify the tool connected to the treatment device, compares the stored value with the value for the phase shift which is specific to each tool, and additionally in particular also an amplitude value for the voltage of the periodic, in particular sinusoidal measurement signal or a signal derived therefrom. Furthermore, in the treatment device, for each tool, data is stored concerning the resources or quantities of resources required. Based on these data and the control signal output by the evaluation device, which defines the detected tool, the control device and/or the supply unit controls the operational parameters and/or dispensing of the resources or quantities of resources.

In accordance with one embodiment, a medical or dental tool comprises a tool shaft and a working end connected to the tool shaft for working on a treatment site, wherein the tool shaft has at least one electrically conductive identification element in which due to an electromagnetic, in particular inductive coupling between the tool and a measuring coil supplied with periodic, in particular sinusoidal electrical energy (alternating current), an alternating electric current and/or electrical eddy currents is induced, which preferably feeds back onto or influences the periodic, in particular sinusoidal electrical energy flowing in the at least one measuring coil to generate the periodic, in particular sinusoidal measurement signal which can be assigned to the respective tool, in particular by mutual inductance and/or ohmic losses.

Having regard to preferred features of the medical or dental tool, in particular the at least one electrically conductive identification element, the base material, etc., reference should be made to the foregoing in order to avoid repetition. Each of the features of the medical or dental tool mentioned and described therein can be applied to or transferred to the medical or dental tool cited herein, either individually or in combination.

Preferably, a set of a plurality of medical or dental tools is provided, in particular as described above, wherein the electrically conductive identification elements of the plurality of tools differ in at least one of the following parameters: the axial length of the electrically conductive identification element with respect to the longitudinal axis of the tool shaft; the cross-sectional areas of the electrically conductive identification elements; the thicknesses of the electrically conductive identification elements transversely to or radially to a longitudinal axis of the tool shaft; the layer thicknesses of the electrically conductive identification elements deposited on the tool shafts; the materials of the electrically conductive identification elements; the number of turns and/or lengths of the electrically conductive identification elements configured as coils or windings; or the wire diameter of the electrically conductive identification elements configured as coils or windings.

Preferably, the plurality of tools, in particular the tool shafts, differ in at least one of the following parameters: the base material of the tool shaft; the diameter of the tool shaft; or the length of the tool shaft. In order to avoid repetition, reference should be made to the foregoing with respect to preferred features of the medical or dental tools of the set of tools, in particular of the at least one electrically conductive identification element, the base material etc. Each of the features of the medical or dental tool mentioned and described therein may be applied to or transferred to the medical or dental tools of the set of tools, individually or in combination.

These and other embodiments will be described below with reference to the following drawings.

DETAILED DESCRIPTION

Figure 1:
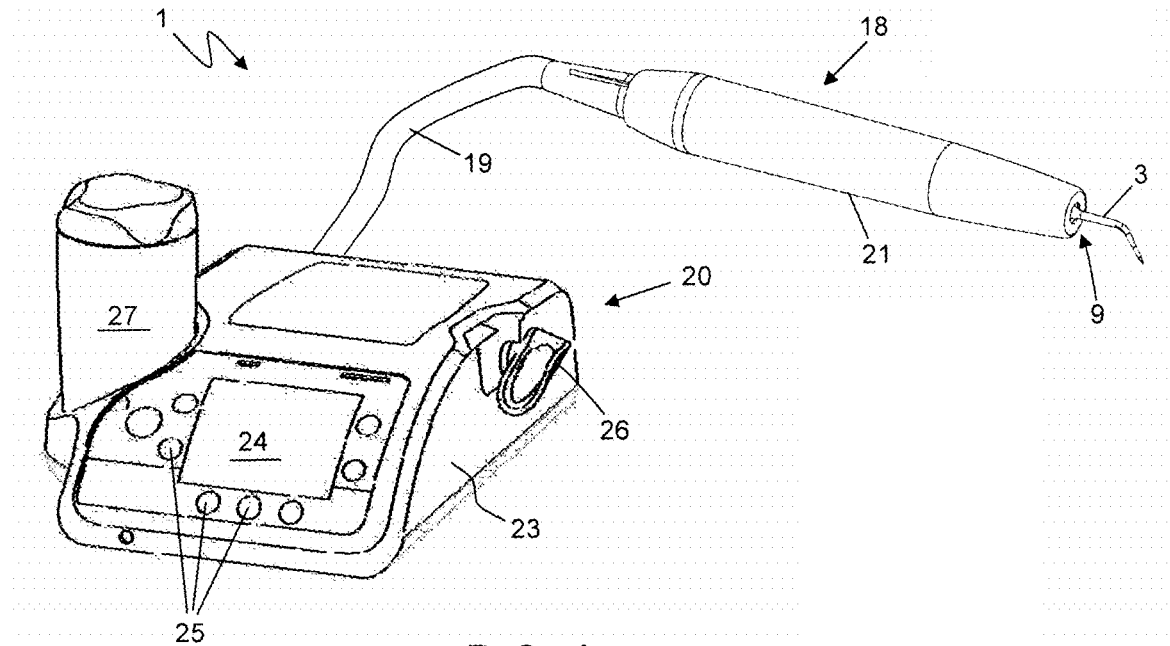
FIG. 1 shows an embodiment of a medical or dental treatment device with an evaluation device for detecting whether a tool is connected to the treatment device or which of a plurality of tools is connected to the treatment device, and a handle element for tartar removal.

The medical or dental treatment device 1 shown in FIG. 1 is configured as a tartar removal device or a scaling device. It comprises a handle element or handpiece 18, a control device or a control unit 20 and a supply or connection tube 19 connecting the control unit 20 and the handpiece 18.

The preferably straight elongate handpiece 18 shown in FIG. 2 has a hollow cylindrical outer sleeve 21 in which, as will be described below in detail, the following are disposed, inter alia: the drive unit 2 for tools 3 which can be connected to the handpiece 18, at least parts of the evaluation device 4 for detecting whether a tool is connected to the treatment device or which of a plurality of tools is connected to the treatment device (see FIG. 3, also termed the tool detecting device 4 below), a tool receiving device or tool retainer 22 for detachably accommodating a plurality of different tools 3, and an illumination device 9 which preferably encircles the tool retainer 22. The control device or control unit 20 has a housing 23 with a display 24 for displaying fixed or adjustable operational parameters or the tool 3 detected by the tool detecting device 4, one or more actuators 25, such as pushbuttons, for selecting or changing operational parameters, a handpiece rest 26 and a source of liquid 27 with a cooling or rinsing liquid.

Figure 3:
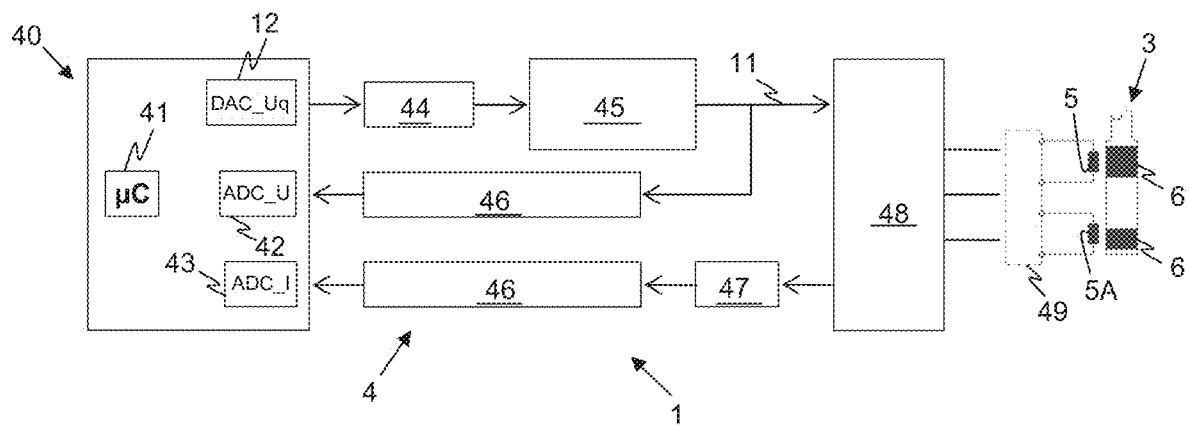
FIG. 3 shows a schematic view of an embodiment of a circuit diagram of a medical or dental treatment device with an evaluation device for detecting whether a tool or which of a plurality of tools is connected to the treatment device.

The power or connecting tubing 19 comprises a plurality of media lines or lines for resources, in particular electrical lines which connect the drive unit 2 and the tool detecting device 4 to an electrical energy supply device 12 (see FIG. 3). A media line 30 connects the liquid source 27 to the tool retainer 22 and a tool 3 accommodated therein, so that liquid can be dispensed via a liquid dispensing opening 28 of the tool 3 onto the treatment side and/or the tool 3, in particular its working end 3A.

Figure 2:
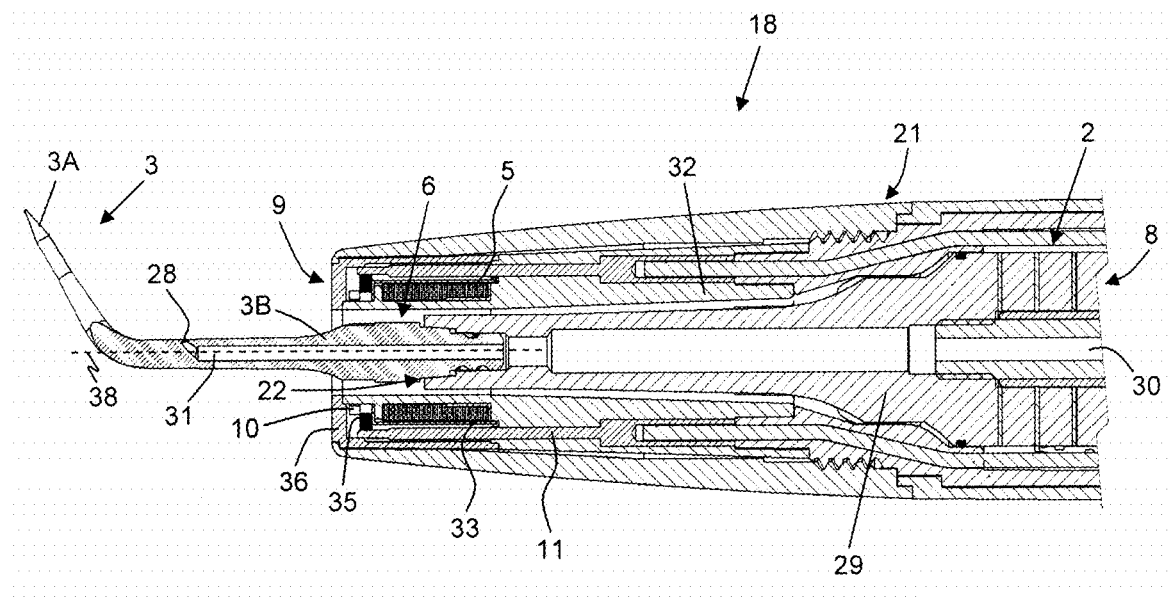
FIG. 2 shows a sectional view of the tool side end of the handle element for tartar removal of FIG. 1.

As can be seen in FIG. 2, the drive unit 2 comprises a vibration generator 8 which is preferably a piezoelectric vibration generator with a plurality of piezoelectric elements. The vibration generator 8 is connected to the tool 3 in order to transmit vibrations via a sonotrode 29, which in particular is designed as a hollow vibrating shaft. At one end of the sonotrode 29, the tool retainer 22 is designed for detachable accommodation of a plurality of tools 3. The tool retainer 22 comprises an internal thread, for example, which can be connected to an external thread of the tool 3, which in particular is provided on its tool shaft 3B. The tool retainer 22 may additionally or alternatively have a conical friction surface, which forms a frictional connection with a second conical friction surface of the tool 3, which in particular is provided on its tool shaft 3B.

The media line 30 connected to the liquid source 27 opens into the hollow sonotrode 29, from which the cooling liquid is transferred into a channel 31 of the tool 3 in order to discharge through the liquid dispensing opening 28.

The sonotrode 29, the tool retainer 22 and a tool shaft 3B of a tool accommodated therein are surrounded by the illumination device 9 at the tool side end of the handpiece 18.

Figure 4:
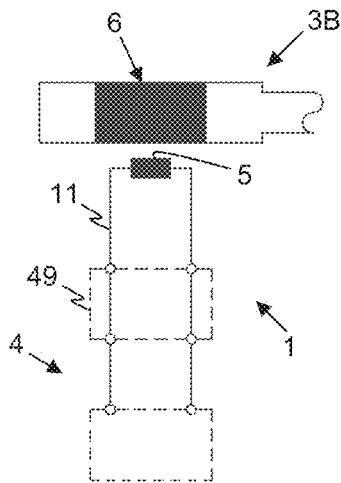
FIG. 4 shows a further schematic view of an embodiment of a circuit diagram for a medical or dental treatment device with an evaluation device for detecting whether a tool or which of a plurality of tools is connected to the treatment device.
Figure 5:
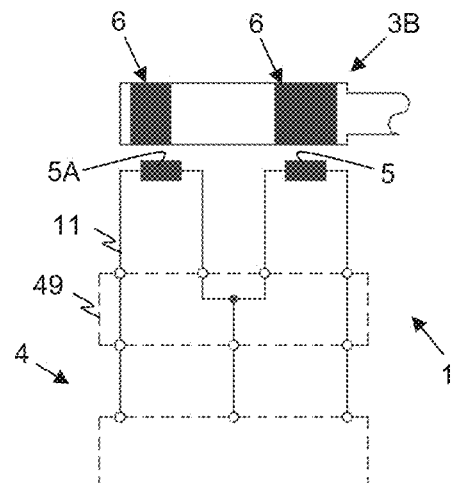
FIG. 5 shows a schematic view of a further embodiment of a circuit diagram for a medical or dental treatment device with an evaluation device for detecting whether a tool or which of a plurality of tools is connected to the treatment device.

Furthermore, at least one preferably cylindrical measuring coil 5, 5A is provided at the tool side end of the handpiece 18 and forms part of the tool detecting device 4 (see also FIGS. 3-5). The at least one measuring coil 5, 5A in particular surrounds at least one section of the tool retainer 22 or is disposed adjacent to the tool retainer 22. The at least one measuring coil 5, 5A is preferably disposed in the handpiece 18 such that when a tool 3 is accommodated in the tool retainer 22, an electrically conductive identification element 6 of the tool 3 is positioned close to the at least one measuring coil 5, 5A, in particular within the at least one measuring coil 5, 5A so that, because of an electromagnetic in particular inductive coupling between the tool 3 accommodated in the tool retainer 22, in particular its at least one electrically conductive identification element 6, and the at least one measuring coil 5, 5A supplied with periodic, in particular sinusoidal electrical energy (alternating current) from the electrical energy supply device 12, a periodic, in particular sinusoidal measurement signal can be generated which is specific for each of the plurality of tools 3 and which can be assigned to the respective tool 3 by the evaluation device 4.

The at least one measuring coil 5, 5A is, for example, supported on a support sleeve 32 formed from plastic. Preferably, a magnetic feedback element 33, which in particular consists of sheet metal, surrounds the at least one measuring coil 5, 5A, in particular on its outside and preferably also at least partially on its inside facing the tool shaft 3B and the sonotrode 29. This sleeve-like feedback element 33, which is provided with an opening to the inside, produces a concentration or compaction of the magnetic field lines or an increase in the magnetic flux density, in particular in the at least one electrically conductive identification element 6 of the tool shaft 3B of the tool 3 accommodated in the tool retainer 22, so that detection of the tool 3 by the tool detecting device 4 is facilitated. The magnetic feedback element 33 in particular also supports the detectability of a plurality of electrically conductive identification elements 6.

Preferably, the at least one measuring coil 5, 5A, in particular also the feedback element 33, is encapsulated by an encapsulation material, for example a resin, in particular epoxy resin, in order to protect it from external influences and contamination and to ensure stability of form.

The illumination device 9, which can include a circuit board 35 and one or more optical semiconductor elements 10, in particular light-emitting diodes, is disposed distally adjacent to the at least one measuring coil 5, 5A. The circuit board 35 is annular in shape, so that a tool 3 inserted into the tool retainer 22 can protrude through its central opening. A transparent plastic sleeve 36 covers the circuit board 35 and the light-emitting diodes 10 and protects them from contamination and mechanical stresses.

The electrical supply in the handpiece 18 for supplying the at least one measuring coil 5, 5A with electric current from the electrical energy supply device 12, preferably also the illumination device 9, is via an electrical line 11. The electrical line 11 is connected with the electrical energy supply device 12 via an electrical line in the supply or connection tube 19.

The medical or dental treatment device 1 shown in the form of a schematic circuit diagram in FIG. 4 comprises an evaluation device 4 for detecting whether a tool or which of a plurality of tools is connected to the treatment device, with a (single) measuring coil 5 and a (single) electrically conductive identification element 6 on the tool shaft 3B of the tool 3. The measuring coil 5 is connected to the electrical energy supply device 12 and the other components of the evaluation device 4 via an electrical line 11.

The medical or dental treatment device 1 shown in the form of a schematic circuit diagram in FIG. 5 comprises an evaluation device 4 for detecting whether a tool or which of a plurality of tools is connected to the treatment device, with two measuring coils 5, 5A and two mutually separated electrically conductive identification elements 6 on the tool shaft 3B of the tool 3. Preferably, the two electrically conductive identification elements 6 respectively are configured as independent electrical circuits 37. The measuring coils 5 are connected together, to the electrical energy supply device 12 and to the other components of the evaluation device 4 via an electrical line 11.

Preferably, an illumination device 9 is also connected to the electrical energy supply device 12 via the electrical line 11 to supply electricity to the optical semiconductor element 10. Preferably, the electrical line 11 can be connected or is connected to an electrical energy supply device 12 in order to supply direct current to the illumination device 9 and to supply the coil of the tool detecting device 4 with alternating current. In order for the electrical line 11 to be able to supply the illumination device 9 with direct current and the at least one measuring coil 5 with alternating current, the alternating current is modulated to direct current or the two voltages are superimposed on each other. Alternatively, it is also possible to supply the illumination device 9 with alternating current from the electrical energy supply device 12 via the electrical line 11.

Preferably, the illumination device 9, in particular at least one optical semiconductor element 10, is disposed on a support 49, for example the circuit board 35. Particularly preferably, the support 49 is also a part of the tool detecting or evaluation device 4 and is, for example, connected to the coil ends of the at least one measuring coil 5 or carries at least one element of the evaluation device 4.

FIG. 3 shows, in the form of a schematic circuit diagram, the construction of the tool detecting device 4, in particular of FIG. 5, in more detail.

The evaluation device 4 for detecting whether a tool or which of a plurality of tools is connected to the treatment device 1 comprises a microcontroller unit 40 which, for example, is disposed in the control device or the control unit 20 or forms at least a part of the control device or the control unit 20. The microcontroller unit 40 comprises a microcontroller 41, the electrical energy supply device 12 to supply the at least one measuring coil 5, preferably also the illumination device 9 with electricity, a device for measuring the voltage 42 and a device for measuring the current 43, preferably indirectly via a voltage measurement. These elements 12, 42, 43 mentioned are preferably configured as a part of the microcontroller 41 and/or are controlled via the microcontroller 41 by software.

The device for measuring voltage 42 and the device for measuring current 43 are in particular provided such that the electrical voltage and the electric current (value) of the periodic, in particular sinusoidal measurement signal received from the at least one measuring coil 5 can be determined, from which the phase shift for detecting whether a tool or which of a plurality of tools is connected to the treatment device 1 can be determined. Preferably, the device for measuring voltage 42 is also intended, for the purposes of tool detection, to determine the amplitude, in particular the extreme values of the amplitude, of the electrical voltage of the periodic, in particular sinusoidal measurement signal.

Preferably, between the at least one measuring coil 5 and the electrical energy supply device 12 are further electrical or electronic components, for example a filter 44 for filtering or smoothing (the high frequency transients caused by the microcontroller of the electrical energy supply device 12 of) the periodic, in particular sinusoidal electrical energy provided by the electrical energy supply device 12 and/or an amplifier 45 to amplify the periodic electrical energy (of the alternating current).

A device for adjusting the level of the voltage and/or a filter 46 protect the microcontroller unit 40 and its components from voltages of the periodic, in particular sinusoidal measurement signal transmitted by the at least one measuring coil 5 which are too high. A current-voltage transformer 47 determines the value of the voltage of the periodic, in particular sinusoidal measurement signal from the measured value of the current of the periodic, in particular sinusoidal measurement signal.

Since the treatment device 1 of FIG. 3 has two measuring coils 5, 5A, but only one evaluation device 4 or microcontroller unit 40, it is necessary, in order to detect the tool, to supply the two measuring coils 5, 5A sequentially with periodic, in particular sinusoidal electrical energy (alternating current). To this end, a switching device 48 is provided which is electrically connected to the respective two coil ends of the two measuring coils 5, 5A, and is configured to supply the two measuring coils 5, 5A sequentially with the periodic, in particular sinusoidal electrical energy from the electrical energy supply device 12 and in particular also to connect to the microcontroller unit 40, the microcontroller 41, the voltage measurement device 42 and/or the current measurement device 43. The switching device 48 is preferably disposed on the support 49 (see also FIG. 5).

The switching device 48 is clearly an optional element which, for example, is not necessary when the treatment device 1 has only one measuring coil 5 (see FIG. 4) or when the treatment device 1 has a plurality of measuring coils 5, 5A and comprises for each coil of the plurality of measuring coils 5, 5A at least one independent device for measuring voltage 42 and one independent device for measuring current 43 or an independent microcontroller unit 40.

FIGS. 6 to 12 show various tools 3 which in particular are provided for use with a treatment device 1. Two or more or all of the tools shown may form a set of tools. Each of the depicted tools has at least one electrically conductive identification element 6 so that it can be identified by the evaluation device 4 for detecting whether a tool is connected to the treatment device 1 or which of a plurality of tools is connected to the treatment device 1. The electrically conductive identification element 6 is a separate element provided on a base material 7 of each tool on the tool shaft 3B.

Figure 6:
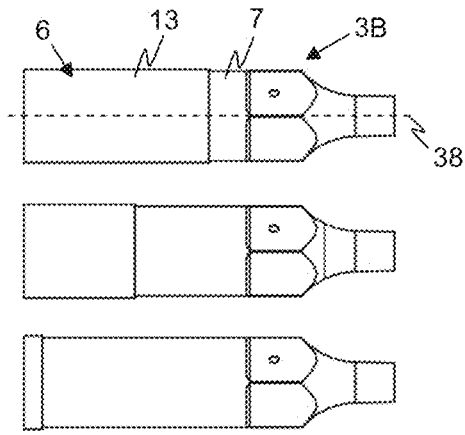
FIG. 6 shows a plurality of tools or a set of tools with a plurality of tools each with an electrically conductive identification element in the form of at least one winding.

In the tools of FIG. 6, the electrically conductive identification element 6 is respectively configured as a winding 13. The windings 13 in particular respectively comprise only a single turn. The windings 13 in particular are each configured as a closed electrical circuit 37 (see also FIG. 12), in which an alternating current flowing about the tool shaft 3B and/or the longitudinal axis 38 of the tool shaft 3B can be induced. The windings 13 of the three different tools of FIG. 6 differ in particular in their axial lengths (with respect to the longitudinal axis 38), so that they produce different phase shifts and/or amplitudes of the periodic, in particular sinusoidal measurement signal and thus can be distinguished by the evaluation device 4. Because of the large axial extent of the single turn of the winding 13, at least some of the windings 13 of the various tools 3 form sleeves or sleeve-like elements. Clearly, the windings 13 may also differ in further properties, in particular those mentioned above, for example in their material, their thickness and/or their radial extent (with respect to the longitudinal axis 38).

Figure 7:
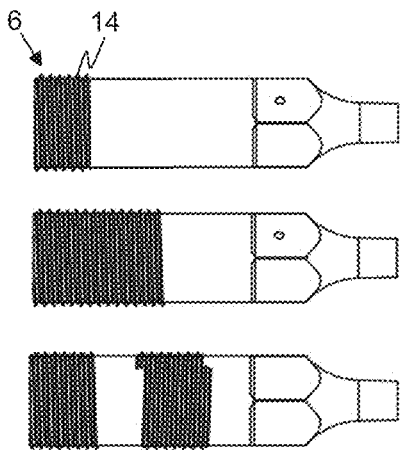
FIG. 7 shows a plurality of tools or a set of tools with a plurality of tools each with an electrically conductive identification element in the form of at least one coil.

In the tools of FIG. 7, the electrically conductive identification element 6 is respectively configured as a coil 14. The coil 14 may, for example, have an insulated winding wire or a flexible printed circuit board. In particular, the coils 14 comprise a plurality of turns. The coils 14 are in particular respectively configured as a closed electrical circuit 37, in which an alternating current flowing about the tool shaft 3B and/or the longitudinal axis 38 of the tool shaft 3B can be induced. The coils 14 of the three different tools of FIG. 7 differ in particular in their axial lengths (with respect to the longitudinal axis 38) and/or in the number of turns and also in the number of coils 14. While the first two tools 3 each have only one coil 14, the third tool 3 has two axially separated coils 14 for detection through the evaluation device 4. Clearly, the coils 14 may also differ from each other in other properties, in particular those mentioned above, for example in their material and/or their cross-sectional areas.

Figure 8:
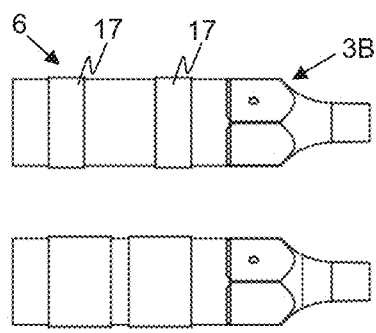
FIG. 8 shows a plurality of tools or a set of tools with a plurality of tools each with an electrically conductive identification element in the form of at least one film.

In the tools of FIG. 8, the electrically conductive identification element 6 is respectively formed as a film 17, wherein respectively, two separated films 17 are disposed on one tool shaft 3B. In particular, the films are each configured as a closed electrical circuit 37, in which an alternating current flowing around the tool shaft 3B and/or the longitudinal axis 38 of the tool shaft 3B can be induced. The films 17 of the various tools of FIG. 8 differ in particular in their axial lengths (with respect to the longitudinal axis 38), so that they produce different phase shifts and/or amplitudes of the periodic, in particular sinusoidal measurement signal and thus can be distinguished by the evaluation device 4. Because of the large axial extent of the films 17, at least some of these films 17 of the various tools form sleeves or sleeve-like elements. Clearly, the films 17 may also differ from each other in other properties, in particular those mentioned above, for example in their material, in their thickness and/or in their radial extent (with respect to the longitudinal axis 38).

Figure 9:
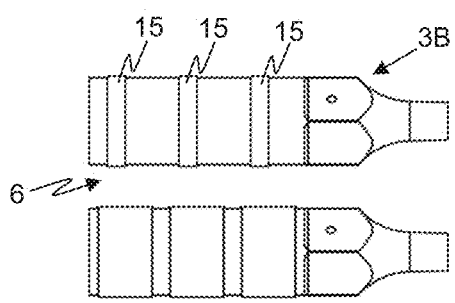
FIG. 9 shows a plurality of tools or a set of tools with a plurality of tools each with an electrically conductive identification element in the form of at least one coating.

In the tools of FIG. 9, the electrically conductive identification element 6 is respectively configured as a coating 15, wherein respectively three axially separated coatings are disposed on one tool shaft 3B. The coatings 15 are in particular respectively configured as a closed electrical circuit 37 in which an alternating current flowing around the tool shaft 3B and/or the longitudinal axis 38 of the tool shaft 3B can be induced. The coatings 15 of the various tools of FIG. 9 again differ in particular in their axial lengths (with respect to the longitudinal axis 38), so that they produce different phase shifts and/or amplitudes of the periodic, in particular sinusoidal measurement signal and thus can be distinguished by the evaluation device 4. Clearly, the coatings 15 may also differ from each other in other properties, in particular those mentioned above, for example in their material and/or layer thickness.

Figure 10:
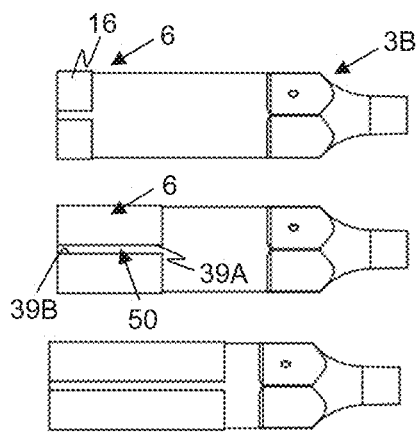
FIG. 10 shows a plurality of tools or a set of tools with a plurality of tools each with an electrically conductive identification element in the form of at least one split sleeve.

In the tools of FIG. 10, the electrically conductive identification element 6 is respectively configured as a sleeve 16, which in particular is split. The split sleeves 16 have two electrically separated ends 39A, 39B which in particular are formed by the gap or slit 50 formed between the two ends 39A, 39B. The split sleeves 16 thus do not form a closed electrical circuit, so that only eddy currents can be induced in the split sleeves 16. The sleeves 16 of the various tools of FIG. 10 again differ in particular in their axial lengths (with respect to the longitudinal axis 38), so that they produce different phase shifts and/or amplitudes of the periodic, in particular sinusoidal measurement signal and thus can be distinguished by the evaluation device 4. Clearly, the coatings 15 may also differ from each other in other properties, in particular those mentioned above, for example in their material, their thickness and/or their radial extent (with respect to the longitudinal axis 38).

Figure 11:
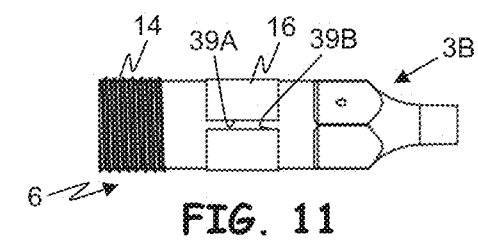
FIG. 11 show a tool with two separated electrically conductive identification elements in the form of a coil and a split sleeve.

The tool of FIG. 11 comprises two different electrically conductive identification elements 6, for example a coil 14 and a split sleeve 16 are shown. Obviously, other electrically conductive identification elements 6 mentioned above may be combined on a tool 3, wherein every possible combination of two or more of the electrically conductive identification elements 6 mentioned above may be envisaged.

Figure 12:
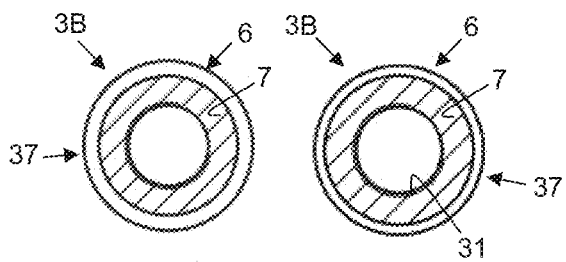
FIG. 12 shows a cross-section through the tool shafts of a plurality of tools, in particular a set of tools, each with an electrically conductive identification element in the form of at least one coating with different layer thicknesses.

Due to the cross-section through the tool shaft 3B of the tools 3 shown in FIG. 12, it is particularly easy to see that the electrically conductive identification elements 6 differ in their thickness, layer thickness and/or radial extent (with respect to the longitudinal axis 38), so that they produce different phase shifts and/or amplitudes of the periodic, in particular sinusoidal measurement signal and thus can be distinguished by the evaluation device 4. Furthermore, it should be noted that the electrically conductive identification elements 6 are configured as a closed electrical circuit 37, in which an alternating current which flows around the tool shaft 3B and/or the longitudinal axis 38 of the tool shaft 3B can be induced. Clearly, the electrically conductive identification elements 6 may also differ in other properties, in particular those mentioned above, for example in their material and/or in their axial extent (with respect to the longitudinal axis 38).

Figure 13:
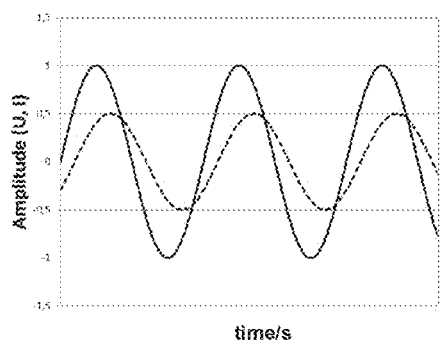
FIG. 13 shows two schematic diagrams with the respective phase shifts and the different amplitudes of two different tools in order to differentiate the tools by the evaluation device.
Figure 13:
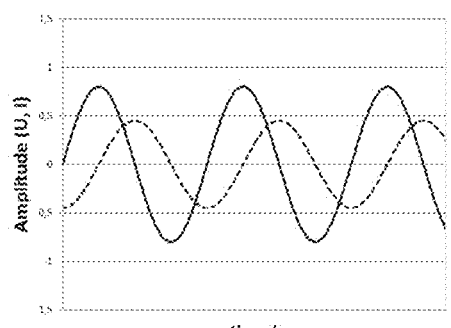

FIG. 13 shows two schematic diagrams each with the phase shifts and the different amplitudes of two different tools 3 for identification of the tools by the evaluation device 4. As described in detail above, the phase shifts and the different amplitudes are in particular produced by the electrically conductive identification element 6 which is specific to each tool 3, preferably additionally by the base material of the tool 3. The phase shift can clearly be seen in both diagrams. The current signal, shown as a dashed line, follows the voltage signal, shown as a solid line, with a temporal shift. The periodic, in particular sinusoidal measurement signals of the two diagrams, i.e., of the two tools detected by the evaluation device 4, differ in their phase shifts and in their amplitudes, in particular the extreme values of the amplitudes or amplitude heights.

The embodiments described or shown in particular serve to illustrate the invention. The features disclosed in one embodiment are therefore not limited to that embodiment, but may be combined individually or together with one or more features of another embodiment.

What is claimed is:

1. A medical or dental treatment device comprising:
a first tool, of a plurality of tools, having a first portion, a second portion and a tool shaft, wherein the first portion of the first tool is an electrically conductive identification element and the second portion of the first tool is an electrically conductive identification element, wherein the first and second electrically conductive identification elements are distinct elements which are arranged spaced apart from one another on the tool shaft;
a tool retainer for connecting to the first tool of the plurality of different tools,
a control unit to induce a periodic or sinusoidal measurement signal of the first portion of the first tool held in the tool retainer and of the second portion of the first tool held in the tool retainer, wherein the control unit comprises an electrical energy supply device and an evaluation device, and
a plurality of measuring coils which are connected to the electrical energy supply device via electrical lines and which are supplied with a periodic or sinusoidal electrical energy supply from the electrical energy supply device, wherein
the evaluation device is electrically connected to the plurality of measuring coils,
wherein due to an inductive coupling between the plurality of measuring coils supplied with the periodic electrical energy and the respective first portion and second portion of the first tool held in the tool retainer, the periodic or sinusoidal measurement signals of the first portion of the tool and of the second portion of the tool are generated, wherein the periodic or sinusoidal measurement signals of the first portion and the second portion are distinct signals and specific to the first tool held in the tool retainer and are assignable to the first tool by the evaluation device, and wherein
the evaluation device determines and processes a phase shift of the electrical voltage and of the electric current of at least one of the periodic or sinusoidal measurement signals to detect the first tool held in the tool retainer.

2. The medical or dental treatment device according to claim 1, wherein the evaluation device further determines an amplitude of the electrical voltage of at least one of the periodic or sinusoidal measurement signals to detect that the first tool of the plurality of tools is connected to the tool retainer.

3. A medical or dental treatment device according to claim 2, wherein the evaluation device determines the phase shift and the amplitude of the electrical voltage of the same periodic or sinusoidal measurement signal.

4. The medical or dental treatment device according to claim 1, wherein the first and second electrically conductive identification elements are provided on a base material of the tool shaft, wherein the first and second electrically conductive identification element and the base material comprise different materials.

5. The medical or dental treatment device according to claim 1, wherein the first and second electrically conductive identification elements on the tool shaft of the at least one tool are separated from one another and form independent electrical circuits.

6. The medical or dental treatment device according to claim 1, wherein each measuring coil of the plurality of measuring coils is associated with one of the first and second electrically conductive identification elements when the tool is accommodated in the tool retainer.

7. The medical or dental treatment device according to claim 1, wherein
the medical or dental treatment device is configured to supply the plurality of measuring coils temporally sequentially with periodic electrical energy, so that a plurality of temporally offset periodic sinusoidal measurement signals can be produced.

8. The medical or dental treatment device according to claim 1, wherein
the medical or dental treatment device is configured to supply the plurality of measuring coils simultaneously with periodic electrical energy in order to produce a plurality of periodic measurement signals.

9. The medical or dental treatment device according to claim 1, wherein
the medical or dental treatment device further comprises a switching device which is electrically connected to the plurality of measuring coils and is configured to supply each measuring coil of the plurality of measuring coils sequentially with the periodic electrical energy.

10. The medical or dental treatment device according to claim 1, wherein the tool shaft comprises steel and the first and second electrically conductive identification elements comprise copper.

11. The medical or dental treatment device according to claim 1, wherein the electrical energy supply device is configured to provide the plurality of measuring coils with periodic or sinusoidal electrical energy at different frequencies so that, in order to detect the first tool, the plurality of measuring coils are configured to be supplied with periodic or sinusoidal electrical energy at different frequencies.

12. The medical or dental treatment device according to claim 1, wherein the first and second electrically conductive identification elements are provided on a base material of the tool shaft and comprises a galvanic coating of an electrically conductive metallic material, and wherein the base material and the electrically conductive metallic material comprise different materials.

13. The medical or dental treatment device according to claim 12,
wherein the different materials comprise steel for the base material of the tool shaft and copper for the galvanic coating.

14. The medical or dental treatment device according to claim 1, wherein the first portion and the second portion each form a closed electrical circuit surrounding the tool shaft.

15. A medical or dental treatment device comprising:
a first tool, of a plurality of tools, having a first portion, a second portion and a tool shaft, wherein the first portion of the first tool is an electrically conductive identification element and the second portion of the first tool is an electrically conductive identification element, wherein the first and second electrically conductive identification elements are distinct elements which are arranged on the tool shaft;
a tool retainer for connecting to the first tool,
a control unit to induce a first periodic or sinusoidal measurement signal of the first portion of the first tool and a second periodic or sinusoidal measurement signal of the second portion of the first tool, wherein the control unit comprises an electrical energy supply device and an evaluation device, and
a first measuring coil and a second measuring coil which are connected to the electrical energy supply device via electrical lines, wherein
while the first tool is retained in the tool retainer, the electrical energy supply device supplies the first measuring coil with a first periodic or sinusoidal electrical energy supply and the second measuring coil with a second periodic or sinusoidal electrical energy supply, so that the first periodic or sinusoidal measurement signal is produced due to inductive coupling between the first portion of the first tool and the first measuring coil and the second periodic or sinusoidal measurement signal is produced due to inductive coupling between the second portion of the first tool and the second measuring coil, wherein the first and second periodic or sinusoidal measurement signals are distinct signals, and wherein
the evaluation device electrically connected to the first and second measuring coils detects that the first tool of the plurality of tools is connected to the tool retainer based on the first and second periodic or sinusoidal measurement signals which together are specific to the first tool and which are assignable to the first tool by the evaluation device.

16. The medical or dental treatment device according to claim 15, wherein the evaluation device determines a phase shift of the electrical voltage and of the electric current of at least one of the first and second periodic or sinusoidal measurement signals to detect that the first tool of the plurality of tools is connected to the tool retainer.

17. The medical or dental treatment device according to claim 15, wherein the evaluation device determines an amplitude of the electrical voltage of at least one of the first and second periodic or sinusoidal measurement signals to detect that the first tool of the plurality of tools is connected to the tool retainer.

18. The medical or dental treatment device according to claim 15, wherein
the electrical energy supply device comprises a switching device which is electrically connected to the first and second measuring coil and is configured to supply the first and second measuring coil sequentially with the periodic or sinusoidal electrical energy while the first tool is retained in the tool retainer.

19. The medical or dental treatment device according to claim 15, wherein the electrical energy supply device is configured to provide the first and second measuring coils with periodic or sinusoidal electrical energy at different frequencies to detect the first tool.

* * * * *